(12) United States Patent
Cohen

(10) Patent No.: US 8,163,297 B2
(45) Date of Patent: Apr. 24, 2012

(54) LIVE ATTENUATED ALDOLASE-NEGATIVE BACTERIAL VACCINE

(75) Inventor: Paul S. Cohen, Narragansett, RI (US)

(73) Assignee: Board of Governors for Higher Education, State of Rhode Island and Providence Plantations, Kingston, RI (US)

( * ) Notice: Subject to any disclaimer, the term of this patent is extended or adjusted under 35 U.S.C. 154(b) by 0 days.

(21) Appl. No.: 13/035,137

(22) Filed: Feb. 25, 2011

(65) Prior Publication Data

US 2011/0195092 A1    Aug. 11, 2011

Related U.S. Application Data

(62) Division of application No. 10/569,396, filed as application No. PCT/US2004/027897 on Aug. 26, 2004, now abandoned.

(60) Provisional application No. 60/498,961, filed on Aug. 29, 2003, provisional application No. 60/498,988, filed on Aug. 29, 2003.

(51) Int. Cl.
*A61K 39/112* (2006.01)

(52) U.S. Cl. .................................................. 424/258.1
(58) Field of Classification Search .................... None
See application file for complete search history.

(56) References Cited

OTHER PUBLICATIONS

Sweeney, N.J., et al., "*Escherichia coli* F-18 and *E. coli* K-12 eda Mutants . . . " Infection and Immunity, Sep. 1996, V64, N9, p. 3504-3511.
Allen, J.H., et al., "A Functional cra Gene Is Required for Salmonella enterica *Serovar typhimurium* . . . " Infection and Immunity, Jun. 2000, V68, N6, p. 3772-3775.
Datsenko, K.A., et al., "One-step inactivation of chromosomal genes in *Escherichia coli* K-12 using PCR products" PNAS, Jun. 2, 2000, V97, N12, p. 6640-6645.

*Primary Examiner* — Gary B. Nickol
*Assistant Examiner* — Nina Archie
(74) *Attorney, Agent, or Firm* — William M. Blackstone

(57) ABSTRACT

The present invention relates to live attenuated bacteria for use in a medicament. The invention also relates to vaccines based upon such bacteria useful for the prevention of microbial pathogenesis and to the use of such bacteria for the manufacture of a vaccine. Finally, the invention relates to methods for the preparation of such vaccines.

5 Claims, No Drawings

SEQUENCE LISTING

```
<160> NUMBER OF SEQ ID NOS: 2

<210> SEQ ID NO 1
<211> LENGTH: 780
<212> TYPE: DNA
<213> ORGANISM: Salmonella typhimurium
<220> FEATURE:
<221> NAME/KEY: CDS
<222> LOCATION: (85)..(726)

<400> SEQUENCE: 1
aaaagctgtc gggtgcggag cagggcgcaa cctgtatcac tttttaagat gacacactag        60
taatcaggcg agagaagaat tccg atg aaa aac tgg aaa aca agt gca gaa          111
                          Met Lys Asn Trp Lys Thr Ser Ala Glu
                          1               5 gca atc ctg acc acc ggc ccg gtt gtc ccg gtc att gta gtc aat aaa         159
Ala Ile Leu Thr Thr Gly Pro Val Val Pro Val Ile Val Val Asn Lys
 10              15                  20                  25 ctg gag cac gcg gtg ccg atg gct aaa gcg ctg gtg gcc ggg ggc gtt         207
Leu Glu His Ala Val Pro Met Ala Lys Ala Leu Val Ala Gly Gly Val
                 30                  35                  40 cgc gtt ctg gaa gtg act tta cgt acg gcc tgc gcg atg gat gct att         255
Arg Val Leu Glu Val Thr Leu Arg Thr Ala Cys Ala Met Asp Ala Ile
             45                  50                  55
```

```
cgc gct atc gct aaa gaa gtg ccg gaa gcg att gtc ggc gcc gga acc        303
Arg Ala Ile Ala Lys Glu Val Pro Glu Ala Ile Val Gly Ala Gly Thr
        60                  65                  70 gtt ctc aat ccg cag cag ttg gcg gag gtg acg gaa gcg ggc gcg caa        351
Val Leu Asn Pro Gln Gln Leu Ala Glu Val Thr Glu Ala Gly Ala Gln
 75                  80                  85 ttt gcg att agc ccg gga ctg act gag cca ctg ctg aaa gcc gcg acg        399
Phe Ala Ile Ser Pro Gly Leu Thr Glu Pro Leu Leu Lys Ala Ala Thr
 90                  95                 100                 105 gca ggc act atc cca ttg att ccc ggt att agc acc gtt tct gaa ctg        447
Ala Gly Thr Ile Pro Leu Ile Pro Gly Ile Ser Thr Val Ser Glu Leu
                110                 115                 120 atg ttg ggc atg gac tat ggt ctg aaa gag ttc aaa ttc ttc ccg gcg        495
Met Leu Gly Met Asp Tyr Gly Leu Lys Glu Phe Lys Phe Phe Pro Ala
            125                 130                 135 gaa gcg aat ggc ggc act aaa gcg ttg cag gcg att gcc ggt ccg ttc        543
Glu Ala Asn Gly Gly Thr Lys Ala Leu Gln Ala Ile Ala Gly Pro Phe
        140                 145                 150 tct cag gta cgt ttc tgc cca act ggc ggc atc tct ccg gca aac tat        591
Ser Gln Val Arg Phe Cys Pro Thr Gly Gly Ile Ser Pro Ala Asn Tyr
    155                 160                 165 cgt gac tat ctg gcg ctg aaa agc gtg ttg tgc atc ggc ggt tcc tgg        639
Arg Asp Tyr Leu Ala Leu Lys Ser Val Leu Cys Ile Gly Gly Ser Trp
170                 175                 180                 185 ctg gtg ccg gcc gac gcg ctg gaa gcg ggt gat tac gat cgc atc acc        687
Leu Val Pro Ala Asp Ala Leu Glu Ala Gly Asp Tyr Asp Arg Ile Thr
                190                 195                 200 aaa ctg gcg cgc gaa gcg gta gaa ggc gcg aag cag taa gccgttaaat        736
Lys Leu Ala Arg Glu Ala Val Glu Gly Ala Lys Gln
            205                 210 gcccgatggc gcttgcttat cgggcttacg agtggcgatc aggc                      780

<210> SEQ ID NO 2
<211> LENGTH: 213
<212> TYPE: PRT
<213> ORGANISM: Salmonella typhimurium

<400> SEQUENCE: 2

Met Lys Asn Trp Lys Thr Ser Ala Glu Ala Ile Leu Thr Thr Gly Pro
 1               5                  10                  15

Val Val Pro Val Ile Val Asn Lys Leu Glu His Ala Val Pro Met
                20                  25                  30

Ala Lys Ala Leu Val Ala Gly Gly Val Arg Val Leu Glu Val Thr Leu
            35                  40                  45

Arg Thr Ala Cys Ala Met Asp Ala Ile Arg Ala Ile Ala Lys Glu Val
    50                  55                  60

Pro Glu Ala Ile Val Gly Ala Gly Thr Val Leu Asn Pro Gln Gln Leu
 65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Ala Gly Thr Ile Pro Leu Ile
            100                 105                 110

Pro Gly Ile Ser Thr Val Ser Glu Leu Met Leu Gly Met Asp Tyr Gly
    115                 120                 125

Leu Lys Glu Phe Lys Phe Phe Pro Ala Glu Ala Asn Gly Gly Thr Lys
130                 135                 140

Ala Leu Gln Ala Ile Ala Gly Pro Phe Ser Gln Val Arg Phe Cys Pro
145                 150                 155                 160
```

-continued

```
Thr Gly Gly Ile Ser Pro Ala Asn Tyr Arg Asp Tyr Leu Ala Leu Lys
            165             170             175

Ser Val Leu Cys Ile Gly Gly Ser Trp Leu Val Pro Ala Asp Ala Leu
            180             185             190

Glu Ala Gly Asp Tyr Asp Arg Ile Thr Lys Leu Ala Arg Glu Ala Val
        195             200             205

Glu Gly Ala Lys Gln
    210
```

LIVE ATTENUATED ALDOLASE-NEGATIVE BACTERIAL VACCINE

This application is a Division of application Ser. No. 10/569,396 filed Feb. 22, 2006, which is the National Phase entry of International Application PCT/US2004/027897 filed Aug. 26, 2004, which claims priority to U.S. Application 60/498,988 filed Aug. 29, 2003 and U.S. Application 60/498,961 filed Aug. 29, 2003, all of which are incorporated herein by reference in their entirety.

The present invention relates to live attenuated bacteria for use in a medicament, to vaccines based upon such bacteria useful for the prevention of microbial pathogenesis, to the use of such bacteria for the manufacture of a vaccine and to methods for the preparation of such vaccines.

Immunity to microbial pathogenesis is one means by which a warm blooded animal avoids pathogenesis, or suffers a less intense pathogenic state. Incomplete immunity to a given pathogen results in morbidity and mortality in a population exposed to a pathogen. It is generally agreed that vaccines based on live but attenuated micro-organisms (live attenuated vaccines) induce a highly effective type of immune response. Such vaccines have the advantage that, once the animal host has been vaccinated, entry of the microbial pathogen into the host induces an accelerated recall of earlier, cell-mediated or humoral immunity which is able to control further growth of the organism before the infection can assume clinically significant proportions. Vaccines based on a killed pathogen (killed vaccine) are generally conceded to be unable to achieve this type of response. However, vaccines that contain a live pathogen present, depending on the level of attenuation, the danger that the vaccinated host upon vaccination may contract the disease against which protection is being sought.

Vaccines against bacteria belonging to e.g. the closely related families of *Escherichia* and *Salmonella* follow the general rules given above. Many members of these families of bacteria are pathogenic due to the fact that they infect the digestive tract and/or the bladder. The pathogenic effect of these bacteria is closely related to their ability to colonise the mucosal layers of the digestive tract and/or the bladder. It is the phenomenon of colonisation that leads to the prolonged presence of the pathogen in the digestive tract and to a very close contact of the pathogen to the mucosal layers, which can also lead to invasion of other tissues. Thus, at the same time, paradoxically, it's due to the fact that these bacteria colonise the digestive tract and/or the bladder, and thus at the same time cause disease, that the immune system is triggered to develop a certain level of immune response. Consequently, this immune response is developed too late to suppress the pathogenic effect of the colonising bacteria.

It would be desirable to have a live attenuated vaccine against enteric infections, that possesses the immunising attributes of a live micro-organism but that is not capable of causing undesirable side effects upon vaccination.

A first prerequisite for such a vaccine would seem to be its ability to colonise the digestive tract. It is the phenomenon of colonisation that provides a firm trigger of the immune system.

It is an objective of the present invention to provide a live attenuated bacterium that does provide protection against infection with wild-type bacteria.

Surprisingly it was found now that bacterial strains of the genus *Escherichia, Salmonella*, and *Yersinia* having a mutation in the eda gene that prevents the synthesis of functional Eda protein are very well capable of inducing a protective immune response against virulent wild-type bacteria in the host animal. Such mutants are, first of all, safe when used as live attenuated vaccine strains. Moreover, they are capable of preventing colonisation of wild type strains. Merely as an example, when such vaccines are administered to chickens of over two weeks of age they are capable of inducing immunity even to the level that neither the vaccine strain nor the challenge strain can be re-isolated from the cloaca after challenge.

This is indeed against all expectations, since it has been shown that *E. coli* Eda-negative mutants do not colonise the mouse large intestine (Sweeney, N. J. et al., in Infect. & Immun. 64: 3504-3511 (1996)). This is even the case if the mice are previously streptomycin-treated. Such treatment leads to the eradication of all facultative bacteria from the intestines, so that all possible intestinal niches are in principle available. Nevertheless, Eda-negative mutants were shown, contrary to their wild-type counterparts, to be unable to colonise in mice. Thus, Eda-negative mutants were also not expected to colonise the digestive tract of other mammals or poultry, so they consequently were not expected to come into sufficiently close contact with the immune system to trigger it anyway.

Therefore, one embodiment of the present invention relates to a live attenuated bacterium that is not capable to express a functional Eda protein as a result of a mutation in the eda gene, for use in a vaccine.

Additionally, Eda-mutants as described in the invention show a very low pathogenicity, which makes them attractive as vaccine strains.

The eda gene, encoding the Eda protein plays a key role in what is known as the Entner-Doudoroff Pathway. Its gene product, the Eda-protein is an enzyme, also known as 2-keto-3-deoxy-6-phospho-gluconate aldolase (KDPG-aldolase). This enzyme is used in the metabolism of glucuronate, galacturonate and gluconate. Fraenkel, D. G. has described the Entner-Doudoroff pathway in e.g. *E.coli* and *Salmonella* at p. 142-150 in F. C. Neidhardt, J. L. Ingraham, K. B. Low, B. Magasanik, M. Schaechter and H. E. Umbarger (ed.), *Escherichia coli* and *Salmonella typhimurium*: cellular and molecular biology. American Society for Microbiology, Washington D.C. (1987).

Egan et al., have analysed the Entner-Doudoroff pathway in *E. coli* and they have analysed the sequence and localized promoters for the edd-eda operon (Egan et al., J. Bacteriology 174: 4638-4646 (1992)).

The sequence of the DNA encoding Eda of *Salmonella typhimurium* is depicted in SEQ ID NO: 1. The sequence of the Eda protein itself is given in SEQ ID NO: 2.

The fact that eda mutants are not expected to colonise the digestive tract explains why, although such mutants were known in the art, they have never been suggested to be potential live attenuated vaccine candidates.

Due to its key position in carbohydrate metabolism, the eda gene and its gene product Eda are relatively widespread in the bacterial realm. The Eda protein is a highly conserved protein. It can be found in e.g. *Escherichia coli*, in *Salmonella* species, more specifically *Salmonella enterica* species, such as serotype Typhimurium, Enteritidis and Dublin and in *Yersinia* species such as *Y. pestis*.

The mutation can be an insertion, a deletion, a substitution or a combination thereof, provided that the mutation leads to the failure to express a functional Eda protein. A functional Eda protein is understood to be a protein having the regulating characteristics of the wild-type protein. Thus, an Eda protein that is defective in at least one of its functions is considered to be a non-functional Eda protein. More specifically, a non-functional Eda protein would not or to a lesser extend, when compared to its wild-type counterpart, be able to mediate the synthesis of KDPG from pyruvate and glyceraldehyde-3-phosphate and vice versa. As a result, a strain having a non-functional Eda-protein would not or to a lesser extent, when compared to its wild-type counterpart, be able to utilise glucuronate, galacturonate and gluconate.

Live attenuated bacteria for use according to the invention can be obtained in several ways. One possible way of obtaining such bacteria is by means of classical methods such as the treatment of wild-type bacteria having the eda gene with mutagenic agents such as base analogues, treatment with ultraviolet light or temperature treatment.

Strains that do not produce a functional Eda protein can easily be picked up. Such mutants can not utilise glucuronate, galacturonate or gluconate, but they can utilise glucose and galactonate.

They can therefore, on the basis of these specific abilities, very easily be selected in vitro. A detailed description of how to make such a selection has been described by Sweeney, N. J. et al., in Infect. & Immun. 64: 3504-3511 (1996).

The nature of a mutation if caused by classical mutation techniques is unknown. This may be a point mutation which may, although this is unlikely to happen, eventually revert to wild-type. In order to avoid this small risk, transposon mutagenesis would be a good alternative. Mutagenesis by transposon mutagenesis, is also a mutagenesis-technique well-known in the art. This is a mutation accomplished at a localised site in the chromosome. Transposon-insertions can not be targeted to a specific gene. It is however very easy to pick up eda-mutants since they do not grow in vitro without nutrient compensation for lack of Eda activity. Therefore, they can easily be selected from a pool of randomly transposon-mutated bacteria.

A much more attractive way of making mutations, i.e. the introduction of a mutation at a predetermined site, rather deliberately than randomly, is offered by recombinant DNA-technology. Such a mutation may again be an insertion, a deletion, a replacement of one nucleotide by another one or a combination thereof, with the only proviso that the mutated gene no longer encodes functional Eda. Such a mutation can e.g. be made by deletion of a number of base pairs. Even very small deletions such a stretches of 10 base pairs can already render Eda non-functional. Even the deletion of one single base pair may already lead to a non-functional Eda, since as a result of such a mutation, the other base pairs are no longer in the correct reading frame. Each deletion of insertion of a number of base pairs indivisible by three causes such a frame shift. More preferably, a longer stretch is removed e.g. 100 base pairs. Even more preferably, the whole eda gene is deleted.

It can easily be seen, that especially mutations introducing a stop-codon in the open reading frame, or mutations causing a frame-shift in the open reading frame are very suitable to obtain a strain which no longer encodes functional Eda.

All techniques for the construction of Eda-negative mutants are well-known standard techniques. They relate to cloning of the Eda-gene, modification of the gene sequence by site-directed mutagenesis, restriction enzyme digestion followed by re-ligation or PCR-approaches and to subsequent replacement of the wild type eda gene with the mutant gene (allelic exchange or allelic replacement). Standard recombinant DNA techniques such as cloning the eda gene in a plasmid, digestion of the gene with a restriction enzyme, followed by endonuclease treatment, re-ligation and homologous recombination in the host strain, are all known in the art and described i.a. in Maniatis/Sambrook (Sambrook, J. et al. Molecular cloning: a laboratory manual. ISBN 0-87969-309-6). Site-directed mutations can e.g. be made by means of in vitro site directed mutagenesis using the Transformer® kit sold by Clontech. PCR-techniques are extensively described in (Dieffenbach & Dreksler; PCR primers, a laboratory manual. ISBN 0-87969-447-3 and ISBN 0-87969-447-5).

The eda gene comprises not only the coding sequence encoding the Eda protein, but also regulatory sequences such as the promoter. The gene also comprises sites essential for correct translation of the Eda mRNA, such as the ribosome binding site.

Therefore, not only mutations in the coding regions but also mutations in those sequences essential for correct transcription and translation are considered to fall within the scope of the invention.

In a preferred embodiment, the invention relates to live attenuated bacteria of the genera *Escherichia*, *Salmonella* and *Yersinia* for use in a vaccine.

In a more preferred form of the invention, the live attenuated bacterium according to the invention is selected from the group consisting of *S. enterica* serotype *typhimurium*, *enteritidis*, *choleraesuis*, *dublin*, *typhi*, *gallinarum*, *abortusovi*, *abortus-equi*, *pullorum*, *E. coli* or *Y. pestis*. These bacterial genera comprise a large number of species that are pathogenic to both humans and a variety of different animals.

In an even more preferred form thereof, the live attenuated bacterium according to the invention is selected from the group consisting of *S. enterica* serotype typhimurium, enteritidis, gallinarum, pullorum, *E. coli* or *Y. pestis*.

Well-defined and deliberately made mutations involving the deletion of fragments of the eda gene or even the whole gene or the insertion of heterologous DNA-fragments or both, have the advantage, in comparison to classically induced mutations, that they will not revert to the wild-type situation.

Thus, in an even more preferred form, this embodiment of the invention refers to live attenuated bacteria in which the eda gene comprises an insertion and/or a deletion.

Given the large amount of vaccines given nowadays to both pets and farm animals, it is clear that combined administration of several vaccines would be desirable, if only for reasons of decreased vaccination costs. It is therefore very attractive to use live attenuated bacteria as a recombinant carrier for heterologous genes, encoding antigens selected from other pathogenic micro-organisms or viruses. Administration of such a recombinant carrier has the advantage that immunity is induced against two or more diseases at the same time. The live attenuated bacteria for use in a vaccine, according to the present invention provide very suitable carriers for heterologous genes, since the gene encoding the Eda protein can be used as an insertion site for such heterologous genes. The use of the eda gene as an insertion site has the advantage that at the same time the eda gene is inactivated and the newly introduced heterologous gene can be expressed (in concert with the homologous bacterial genes). The construction of such recombinant carriers can be done routinely, using standard molecular biology techniques such as allelic exchange.

Therefore, another embodiment of the invention relates to live attenuated recombinant bacteria, preferably of the genera *Escherichia*, *Salmonella* and *Yersinia* that do not produce a functional Eda protein and in which a heterologous gene is inserted, for use in a vaccine. Such a heterologous gene can, as mentioned above, e.g. be a gene encoding an antigen selected from other pathogenic micro-organisms or viruses. Such genes can e.g. be derived from pathogenic herpesviruses (e.g. the genes encoding the structural proteins of herpesviruses), retroviruses (e.g. the gp160 envelope protein), adenoviruses and the like.

Also a heterologous gene can be obtained from pathogenic bacteria. As an example, genes encoding bacterial toxins such as *Actinobacillus pleuropneumoniae* toxins, *Clostridium* toxins, outer membrane proteins and the like are very suitable bacterial heterologous genes. Another possibility is to insert a gene encoding a protein involved in triggering the immune system, such as an interleukin or an interferon, or another gene involved in immune-regulation.

Insertion of the heterologous gene in the eda gene is advantageous, since in that case there is no need to find a new suitable insertion site for the heterologous gene, and at the same time the eda gene is knocked out.

Thus, in a preferred form of this embodiment the heterologous gene is inserted in the eda gene. The heterologous gene can be inserted somewhere in the eda gene or it can be inserted at the site of the eda gene while this gene has been partially or completely deleted.

Because of their unexpected attenuated but immunogenic character in vivo, the bacteria for use in a vaccine, according to the invention are very suitable as a basis for live attenuated vaccines. Thus, still another embodiment of the invention relates to live attenuated vaccines for the protection of animals and humans against infection with a bacterium of which the wild type form comprises a eda gene.

Such vaccines comprise an immunogenically effective amount of a live attenuated bacterium for use in a vaccine, according to the invention or a live recombinant carrier bacterium according to the invention, and a pharmaceutically acceptable carrier.

Preferably, the vaccine comprises a live attenuated bacterium according to the invention, selected from the group of *Escherichia, Salmonella* and *Yersinia*.

Immunogenically effective means that the amount of live attenuated bacteria administered at vaccination is sufficient to induce in the host an effective immune response against virulent forms of the bacterium.

In addition to an immunogenically effective amount of the live attenuated bacterium described above, a vaccine according to the present invention also contains a pharmaceutically acceptable carrier. Such a carrier may be as simple as water, but it may e.g. also comprise culture fluid in which the bacteria were cultured. Another suitable carrier is e.g. a solution of physiological salt concentration.

The useful dosage to be administered will vary depending on the age, weight and animal vaccinated, the mode of administration and the type of pathogen against which vaccination is sought.

The vaccine may comprise any dose of bacteria, sufficient to evoke an immune response. Doses ranging between $10^3$ and $10^{10}$ bacteria are e.g. very suitable doses.

Optionally, one or more compounds having adjuvant activity may be added to the vaccine. Adjuvants are non-specific stimulators of the immune system. They enhance the immune response of the host to the vaccine. Examples of adjuvants known in the art are Freunds Complete and Incomplete adjuvant, vitamin E, non-ionic block polymers, muramyldipeptides, ISCOMs (immune stimulating complexes, cf. for instance European Patent EP 109942), Saponins, mineral oil, vegetable oil, and Carbopol.

Adjuvants, specially suitable for mucosal application are e.g. the *E. coli* heat-labile toxin (LT) or Cholera toxin (CT).

Other suitable adjuvants are for example aluminium hydroxide, aluminium phosphate or aluminium oxide, oil-emulsions (e.g. of Bayol F® or Marcol 52®), saponins or vitamin-E solubilisate.

Therefore, in a preferred form, the vaccines according to the present invention comprise an adjuvant.

Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Especially when such stabilisers are added to the vaccine, the vaccine is very suitable for freeze-drying. Therefore, in a more preferred form, the vaccine is in a freeze-dried form.

For administration to animals or humans, the vaccine according to the present invention can be given inter alia intranasally, intradermally, subcutaneously, orally, by aerosol or intramuscularly. For application to poultry, wing web and eye-drop administration are very suitable.

The skilled person would know how to administer a vaccine according to the invention, because the method would most likely not differ from the methods followed for vaccination with presently existing bacterial vaccines. A vaccine according to the invention, especially when it comprises bacteria belonging to the family of *E. coli, Salmonella* or *Yersinia* would preferably be given orally.

Still another embodiment relates to the use of a bacterium or a recombinant bacterium according to the invention for the manufacture of a vaccine for the protection of animals and humans against infection with a wild type bacterium or the pathogenic effects of infection.

Still another embodiment of the invention relates to methods for the preparation of a vaccine according to the invention. Such methods comprise the admixing of a live attenuated bacterium according to the invention or a live recombinant carrier bacterium according to the invention, and a pharmaceutically acceptable carrier.

EXAMPLES

Example 1

Construction of Eda-negative mutant.

The eda deletions were made using a modified Wanner method (PNAS June 6, 2000. 97(12):6640-45). Primers to the 5' and 3' eda flanking sequences of *S. enteritidis* SE5609 were designed with PstI sites (PstI eda 5': cta gct gca ggt gct aag cgg taa tct ggg [SEQ ID NO.: 3] and PstI eda 3': cta gct gca gaa gag att gct cgt cat gtg g [SEQ ID NO.: 4]) and the PCR product was cloned into pBluescript SKII+(pBSeda). BglII containing primers, to the eda promoter region (ctag aga tct ctcgcct-gattacta gtgtg[SEQ ID NO.: 5]) and the 3' end (ctag agatct aag ccg ttaaatgcccgatgg [SEQ ID NO.:6]) were used to reverse PCR amplify the flanking and vector sequences from pBSeda. BglII digestion and subsequent ligation created an eda deletion clone called pBSedaΔ. A 1.2 kb BamHI digested chloramphenicol resistant gene was inserted into the BglII site of pBSedaΔ to produce pBSedaΔcam. pBSedaΔcam was digested with PstI and the insert was separated from vector sequences and used as the template for PCR. Eight 100 μl reactions were pooled, 5 μl was checked on a gel, and the linear PCR product was ethanol precipitated and resuspended in 2-4 μl of water.

*S. enteritidis* SE5609 cells were electroporated with the temperature sensitive plasmid pKD46. When these cells are grown at 30° C. in the presence of arabinose the plasmid expresses the lambda Red recombinase. The cells ($A_{600}$=0.6) were made competent for electroporation by centrifugation and washing 3-4× with cold 10% glycerol. The linear PCR product was then electroporated into the competent cells. The recombinase acts to replace the wild type eda gene with the deleted eda gene containing the chloramphenicol cassette.

SE5609 clones containing the deleted eda gene containing the chloramphenicol cassette were selected by overnight growth at 37° C. on Luria agar plates containing chloramphenicol (30 μg/ml), which also resulted in loss of the temperature sensitive pKD46 plasmid.

A different set of flanking eda 5' (ctagctgca gcc tca tat tcc gga cct gag c [SEQ ID NO.: 7]) and eda 3' (cta gct gca ggt gac ggt aaa agg cta atg cg[SEQ ID NO.:8]) primers were used to verify one of the SE5609-eda$^{(-)}$ eda mutants. An amplified fragment containing the wild type SE5609 eda gene produced a 927 bp band as expected, while the eda deletion/chloramphenicol mutant gave the expected 1677 bp product. 1.8 mM MgCl$_2$, with Finnzyme DyNAzymell polymerase was used in the reaction. Cycling conditions were 1×94° C. 4 min; 30×94° C. 15 sec, 55° C. 30 sec, 72° C. 130 sec; 1×72° C. 7 min. In addition, the same SE5609-eda$^{(-)}$ eda mutant was also confirmed by its inability to grow in liquid M9 minimal medium containing 0.2% (w/w) gluconate as the sole carbon source.

Example 2

Safety, Vaccination- and Challenge-Tests
Experimental Design

To test both safety and efficacy, chickens were orally inoculated at 6 and 14 weeks of age with respectively 1.1×10$^8$ CFU and 4.1×10$^8$ CFU of SE5609-eda$^{(-)}$.

Safety was assessed by clinical observation after vaccination. Also, cloaca swabs were taken at days 7 and 14 after each vaccination to determine the presence of the vaccine strain in the intestinal tract. Swabs were used to inoculate Brilliant Green Agars (BGA) directly and after enrichment in Rappaport Vassiliades Broth.

To test for efficacy, the vaccinated chickens and unvaccinated controls received an oral challenge infection with 1.3× 10$^8$ CFU of a naladixic acid resistant wild-type S.e. strain at 16 weeks of age. Cloaca swabs were taken 3, 7 and 14 days after challenge to determine the rate of colonization by the challenge strain. Swabs were inoculated on BGA containing naladixic acid (BGAnal) directly and also after incubation in an enrichment medium (buffered peptone water containing nal).

Animals

Commercial laying hens were obtained from a *Salmonella* free flock.

Results

No clinical abnormalities were observed after both oral vaccinations.

First of all, the SE5609-eda$^{(-)}$ strain was not cultured from cloacal swabs of the vaccinated animals on days 7 and 14, indicating that the strain was impaired in its ability to colonize the digestive tract of chickens.

Moreover, as shown in Table 1, vaccination with SE5609-eda$^{(-)}$ resulted in a very significant reduction in colonization of the digestive tract by the challenge strain.

TABLE 1

Reisolation of the challenge strain from cloaca swabs

| Day post challenge | S.e. (nal$^r$) positive | |
|---|---|---|
| | SE5609-eda | Control |
| 3 | 1/15$^a$ | 11/15 |
| 7 | 1/15$^a$ | 9/14 |
| 14 | 0/15 | 2/14 |

$^a$significantly different from control (p < 0.01, Fisher exact test)

Conclusion: a vaccine based upon a *Salmonella enteritidis* eda$^{(-)}$ strain which is a wild-type strain having eda$^{(-)}$ as a single attenuation is safe. Moreover, vaccination with this *Salmonella enteritidis* eda$^{(-)}$ strain resulted in complete prevention of colonization of the digestive tract by both the vaccine strain and the challenge strain.

---

The invention claimed is:

1. A method for reducing the colonization of the digestive tract of an animal by wild type *Salmonella enterica*, comprising administering to the animal an immunogenically effective amount of a live attenuated bacterium of the species *Salmonella enterica* having a mutation in the eda gene, whereby said bacterium is unable to express a functional 2-keto-3deoxy-6-phospho-gluconate aldolase (KDPG-aldolase) Eda protein.

2. The method according to claim 1, wherein said bacterium is *S. enterica* of a serotype selected from the group consisting of *typhimurium, enteritidis, choleraesuis, dublin, typhi, gallinarum, abortusovi, abortus-equi*, and *pullorum*.

3. The method according to claim 1, wherein the mutation is an insertion and/or a deletion.

4. The method according to claim 1, wherein said bacterium carries a heterologous gene.

5. The method according to claim 4, wherein said heterologous gene is inserted in the eda gene.

* * * * *